(12) United States Patent
Tuneberg

(10) Patent No.: US 6,843,370 B2
(45) Date of Patent: Jan. 18, 2005

(54) PACKAGE FOR PREPASTED ORTHODONTIC BRACKET

(75) Inventor: Lee H. Tuneberg, Sheboygan, WI (US)

(73) Assignee: American Orthodontics, Sheboygan, WI (US)

( * ) Notice: Subject to any disclaimer, the term of this patent is extended or adjusted under 35 U.S.C. 154(b) by 205 days.

(21) Appl. No.: 10/176,368

(22) Filed: Jun. 20, 2002

(65) Prior Publication Data

US 2002/0195363 A1 Dec. 26, 2002

Related U.S. Application Data

(60) Provisional application No. 60/229,640, filed on Jun. 20, 2001.

(51) Int. Cl.$^7$ ............................................. B65D 83/10
(52) U.S. Cl. ...................... 206/369; 206/63.5; 206/460
(58) Field of Search .................... 206/365, 63.5, 206/467, 469, 460, 471, 820, 813, 369, 538

(56) References Cited

U.S. PATENT DOCUMENTS

| | | | |
|---|---|---|---|
| 3,773,250 A | * 11/1973 | Phillips | ................... 229/69 |
| 4,977,003 A | 12/1990 | Brown et al. | |
| 4,978,007 A | 12/1990 | Jacobs et al. | |
| 5,015,180 A | 5/1991 | Randklev | |
| 5,161,969 A | 11/1992 | Pospisil et al. | |
| 5,172,809 A | 12/1992 | Jacobs et al. | |
| 5,221,202 A | 6/1993 | James | |
| 5,279,800 A | 1/1994 | Berry, Jr. | |
| 5,328,363 A | 7/1994 | Chester et al. | |
| 5,348,154 A | 9/1994 | Jacobs et al. | |
| 5,350,059 A | 9/1994 | Chester et al. | |
| 5,354,199 A | 10/1994 | Jacobs et al. | |
| 5,377,823 A | 1/1995 | Steen et al. | |
| 5,429,229 A | 7/1995 | Chester et al. | |
| 5,538,129 A | 7/1996 | Chester et al. | |
| 5,552,177 A | 9/1996 | Jacobs et al. | |
| 5,558,516 A | 9/1996 | Horn et al. | |
| 5,575,645 A | 11/1996 | Jacobs et al. | |
| 5,636,736 A | 6/1997 | Jacobs et al. | |
| 5,697,780 A | 12/1997 | Tuneberg et al. | |
| 5,711,665 A | 1/1998 | Adam et al. | |
| 5,746,594 A | 5/1998 | Jordan et al. | |
| 5,756,174 A | 5/1998 | Tuneberg | |
| 5,762,192 A | 6/1998 | Jacobs et al. | |
| 5,794,774 A | * 8/1998 | Porcelli | ...................... 206/369 |
| 5,810,584 A | 9/1998 | Wong | |
| 5,827,058 A | 10/1998 | Kelly et al. | |
| 6,050,815 A | 4/2000 | Adam et al. | |
| 6,089,861 A | 7/2000 | Kelly et al. | |
| 6,244,442 B1 | * 6/2001 | Inoue et al. | ................. 206/531 |
| 6,696,507 B2 | * 2/2004 | Subelka et al. | ............. 523/115 |
| 2003/0196914 A1 | 10/2003 | Tzou, et al. | |

* cited by examiner

Primary Examiner—Shian T. Luong
(74) Attorney, Agent, or Firm—Philip G. Meyers

(57) ABSTRACT

The invention provides a package for a prepasted orthodontic bracket that includes a cover having a hollow projection thereon and a lateral flange extending from and surrounding an open end of the projection, and a base having a flat upper surface. An orthodontic bracket having a layer of light-curable paste thereon is placed with the paste layer in contact with a flat upper surface of the base. The bracket is surrounded by and spaced from the cover. Each of the cover and base are opaque to visible light and actinic radiation. The cover, or both cover and base, comprise a bilayered plastic structure including a first plastic layer containing particles of an opaque filler in an amount effective to render the first layer opaque to visible light, and a second plastic layer containing an effective amount of an actinic blocking agent.

14 Claims, 1 Drawing Sheet

PACKAGE FOR PREPASTED ORTHODONTIC BRACKET

This application is a conversion of U.S. Provisional Patent Application Ser. No.: 60/299,640, filed Jun. 20, 2001.

FIELD OF THE INVENTION

The present invention relates generally to packaging systems for orthodontic devices, particularly brackets of the type that are pasted onto a patient's teeth.

BACKGROUND OF THE INVENTION

Orthodontic brackets are cemented or pasted onto a patient's teeth. Typically the paste is prepared and applied to the bonding surface of the bracket at the time of use. However, pre-pasted bracket systems have been gaining in popularity. According to such systems, the paste is applied to the bonding surface by the manufacturer, and the pre-pasted bracket is placed in a special package that permits the bracket, with a predetermined quantity of paste attached, to be removed at the time of use. A number of packaging systems have been proposed which provide varying solutions to the problem of removing the pre-pasted bracket without leaving paste behind on the package. Often the prepasted bracket is set in a recess which is then sealed with a cover.

Where the paste is of a type that is cured by exposure to visible light radiation, the packaging should protect the prepasted bracket from curing prematurely. U.S. Pat. No. 4,978,007 describes a packaged element containing (a) a substrate that transmits less than about 0.5% of actinic radiation and has at least one recess, (b) a cover that transmits less than about 0.5% of actinic radiation and transmits at least part of the visible light spectrum, (c) a structure for maintaining the cover in contact with the substrate such that the cover filters incident radiation entering the recess, and (d) an element located in the recess and having a substance thereon that is curable by exposure to the actinic radiation. Cover materials described in the '007 patent include colored transparent films, opaque to the wavelength of light required to cure the paste, but sufficiently transparent to non-curing wavelengths to permit viewing the bracket through the film.

Known systems for storage of prepasted brackets tend to be elaborate, difficult to make structures. Viewing of the bracket may be aesthetically satisfying but is unnecessary, especially when all of the brackets purchased as a set or group are alike. The present invention provides a packaging material and structure that is easier to manufacture, provides better protection for the pasted bracket prior to use, and makes each bracket easier to remove.

SUMMARY OF THE INVENTION

The present invention provides a package for a prepasted orthodontic bracket that includes a cover having a hollow projection thereon and a lateral flange extending from and surrounding an open end of the projection, and a base having a flat upper surface. An orthodontic bracket having a layer of light-curable paste thereon is placed with the paste layer in contact with a flat upper surface of the base. The bracket is surrounded by and spaced from the cover. Each of the cover and base are opaque to visible light and actinic radiation. The cover, or both cover and base, comprise a bilayered plastic structure including a first plastic layer containing particles of an opaque filler dispersed therein in an amount effective to render the first layer opaque to visible light, and a second plastic layer having an effective amount of an actinic blocking agent dispersed therein. In the alternative, a monolayered plastic having both the filler and actinic blocking agent dispersed therein could be used in place of the bilayered plastic structure. As referred to herein, an "actinic blocking agent" refers to a material that specifically absorbs light of a wavelength that cures (polymerizes) the paste, most commonly in the 400–520 nm range, but transmits other light wavelengths and is thus not entirely opaque.

According to another aspect of the invention, a multi package for prepasted orthodontic brackets includes a cover having a series of spaced hollow projections therein and a lateral flange extending from and surrounding open ends of the projections, and a base having a flat upper surface. A series of orthodontic brackets each having a layer of light-curable paste thereon are placed in spaced positions with the paste layer in contact with a flat upper surface of the base, so that each bracket is disposed inside a hollow projection of the cover. A releasable adhesive layer formed on an undersurface of the flange secures the cover to the base. As in the single package embodiment, the cover and base are opaque to visible light and actinic radiation, and at least the cover comprises a bilayered plastic structure including a first plastic layer containing particles of an opaque filler in an amount effective to render the first layer opaque to visible light, and a second plastic layer containing an effective amount of an actinic blocking agent. These and other aspects of the invention are discussed in the detailed description that follows.

BRIEF DESCRIPTION OF THE DRAWING

In the accompanying drawings, like numerals represent like elements except where section lines are indicated.

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention and are not to limit the scope of the invention.

DETAILED DESCRIPTION

Figure 1:
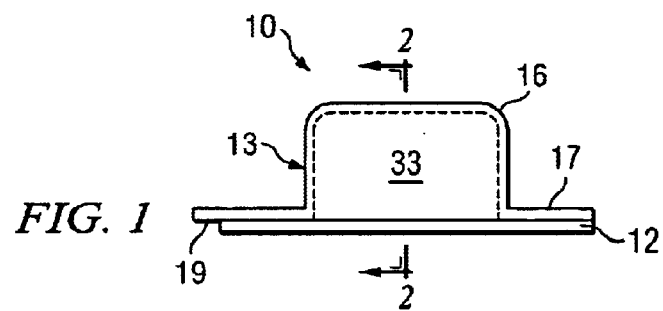
FIG. 1 is side view of a pre-pasted bracket package according to the invention.
Figure 2:
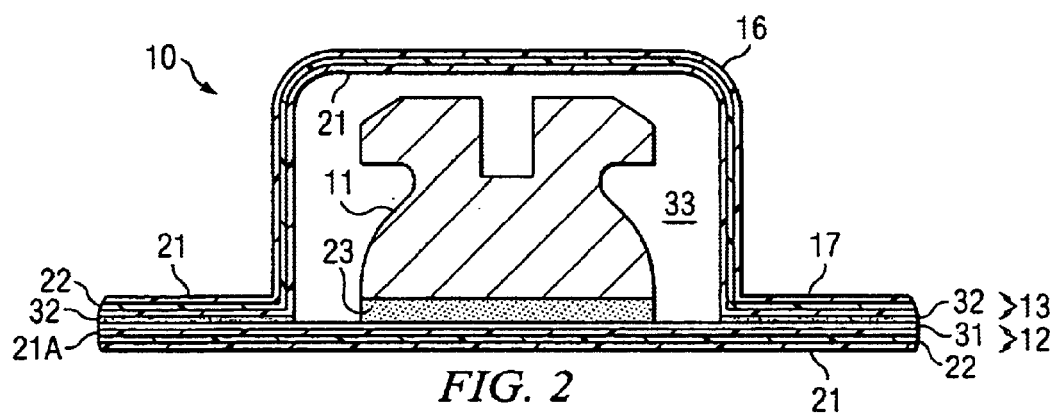
FIG. 2 is a view taken along the line 2—2 in FIG. 1, partly in section.
Figure 3:
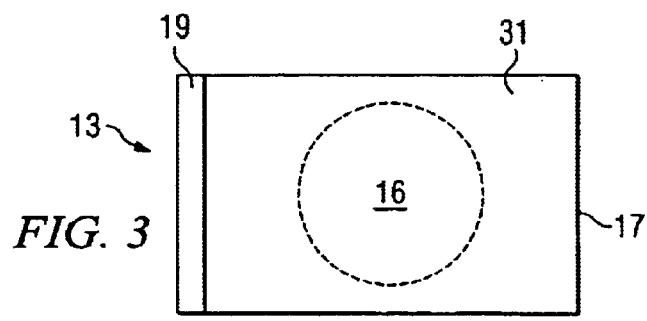
FIG. 3 is a bottom view of the cover of FIG. 1.

Referring to FIGS. 1 to 3, a single package 10 for a pre-pasted bracket 11 includes a flat base 12 and a cover 13. Cover 13 has a central dome or hollow projection 16 forming an internal cavity in which bracket 11 is stored and a flat flange portion 17 extending laterally from projection 16. Flange portion 17 is superposed against an upper surface of base 12 to form an airtight enclosure for bracket 11 as described hereafter. One edge of flange 17 extends beyond base 12 to form a tab 19 to aid in peeling off cover 13 at the time of use.

According to a preferred form of the invention, base 12 and cover 13 are made of the same material to improve the economy of manufacture. A preferred material is a trilayered laminate include top and bottom opaque layers 21 and a middle layer 22 containing a light absorbing agent or actinic blocking agent that specifically absorbs wavelengths of light that cure the paste layer 23 disposed on the underside of bracket 11. The trilayered material may be quite thin, for example, 0.020" inch. Paste layer 23 is made of a typical light-curable orthodontic adhesive such as Eagle No-Drift. In particular, opaque layers 21 preferably comprise a plastic such as polystyrene, polycarbonate, PVC or polyethylene in which particles of an opaque filler are dispersed. A preferred filler is carbon black due to its common availability low cost and black color, though other fillers, such as opaque inorganic oxides, could be used. The amount and particle size of the filler is not essential so long as the resulting plastic has an opaque appearance to an ordinary observer.

The middle layer may be a thin film sandwiched between the thicker layers 21, such as one of the cover materials described in U.S. Pat. No. 4,978,007, the contents of which are incorporated by reference herein. If desired, one the layers 21 may be omitted from each side and the resulting bilayered material can be used. The combination of the opaque filler with the actinic blocking agent ensures that no polymerizing light will enter the package, and provides more effective protection from such radiation than a film containing the blocking agent alone.

A lubricious layer 31, made of a suitable material such as silicone or a high lubricity plastic such as polyethylene or Teflon, is preferably formed on the upper surface of base 12, so that paste 23 tends to remain on bracket 11 when bracket 11 is removed from base 12. As shown in FIG. 2, the underside of flange 17 may be coated with a pressure or heat sensitive adhesive 32 so that the compartment 33 in which bracket 11 is stored remains air tight until the time of use. Coating the entire underside of flange 17 is vastly simpler that coating only selected areas of cover 13. Layer 31, which contacts the adhesive 32, aids in separating cover 13 from base 12 at the time of use. Brackets 11 are placed with the paste 23 in direct contact with the flat upper surface of base 12, specifically in direct contact with layer 31. No special structures such as bumps, ridges, projecting plastic tongues or the like are needed to permit effective removal of the pasted bracket from the base. Manual removal of a bracket 11 from flat base 12 is easier than from a recess or well. As an alternative to layer 31, the high lubricity material may be incorporated into the uppermost layer 21A of base 12. Either method is sufficient to give base 12 a slippery top surface.

Figure 4:
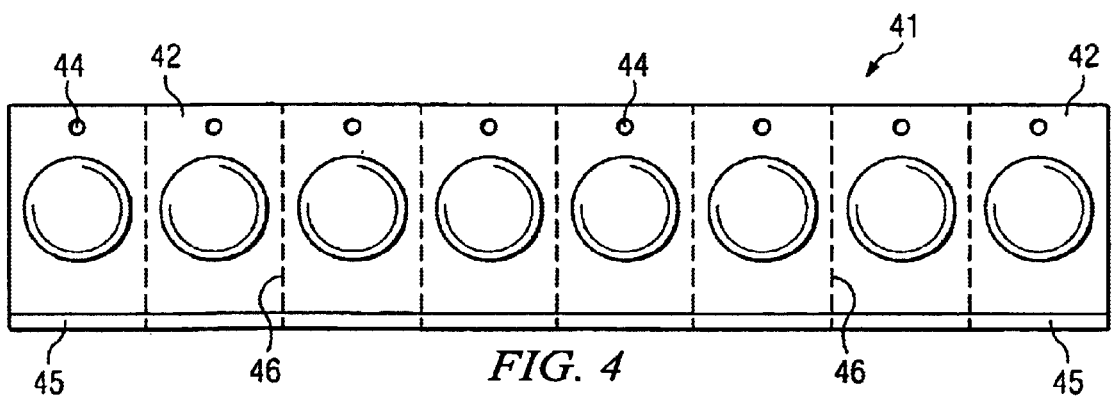
FIG. 4 is a top view of a strip of bracket packages according to the invention.

Packages according to the invention may be made for individual brackets, as in FIGS. 1–3, or may be grouped together in tape or strip form as illustrated in FIG. 4. In FIG. 4, a strip 41 of five or ten prepasted bracket packages 42 each substantially the same as described above in connection with FIGS. 1–3 can be manufactured in the following manner. The base material is formed with a two or more registration holes therein, which may be set over upright pins on a horizontal holder. Optionally, the base may next be moved into an enclosure filled with an inert atmosphere, such as argon or nitrogen gas. Inside the enclosure, a group of prepasted brackets are placed in spaced positions on the lubricious layer 31 of the base. A strip of side-by-side covers 13 with matching holes 44 therein is then placed over the alignment pins, ensuring proper registration between the edges of the base and cover. A peel off tab 45 may be provided by an overhanging edge of the cover strip on the side opposite the alignment holes.

Pressure is applied such that the adhesive 32 seals each compartment 33 with an inert gas trapped therein. The inert gas further aids in preventing deterioration of the paste during storage prior to use. The strip is then removed from the enclosure, and may then be cut into individual packages 10 as described above, or left in strip form. If the latter, score lines or lines of weakness 46 may be provided between individual packages 10 to aid in tearing off one at a time as needed. The resulting strip, if sufficiently flexible, may comprise a tape that can be wound up and unwound as needed when brackets are used.

While certain embodiments of the invention have been illustrated for the purposes of this disclosure, numerous changes in the method and apparatus of the invention presented herein may be made by those skilled in the art, such changes being embodied within the scope and spirit of the present invention as defined in the appended claims.

What is claimed is:

1. A package for a prepasted orthodontic bracket, comprising:

a cover, including a hollow projection therein and a lateral flange extending from and surrounding an open end of the projection;

a base having a flat upper surface; and an orthodontic bracket having a layer of light-curable paste thereon, which bracket is placed with the paste layer in contact with a flat upper surface of the base, and the bracket is surrounded as by and spaced from the cover, wherein each of the cover and base are opaque to visible light and actinic radiation, and wherein the cover comprises a bilayered plastic structure including a first plastic layer containing particles of an opaque filler in an amount effective to render the first layer opaque to visible light, and a second plastic layer containing an effective amount of an actinic blocking agent.

2. The package of claim 1, wherein the bilayered plastic structure further includes a third plastic layer containing particles of an opaque filler in an amount effective to render the third layer opaque to visible light, wherein the second plastic layer is interposed between the first and third plastic layers.

3. The package of claim 1, wherein the base is made of the same bilayered plastic structure as the cover.

4. The package of claim 1, wherein the flat upper surface of the base has a lubricious material thereon, which lubricious material is in contact with the paste of the bracket.

5. The package of claim 1, further comprising a releasable adhesive layer formed on an undersurface of the flange, which adhesive layer secures the cover to the base.

6. The package of claim 5, further comprising a lubricious layer formed on an upper surface of the base, which lubricious layer is in contact with the paste of the bracket and the adhesive layer.

7. The package of claim 1, further comprising a gas inert to the paste surrounding the pasted bracket, wherein the base and cover form a gas-tight, sealed compartment for the pasted bracket.

8. The package of claim 5, further comprising a gas inert to the paste surrounding the pasted bracket, wherein the adhesive layer surrounds the open end of the projection so that the base and cover form a gas-tight, sealed compartment for the pasted bracket.

9. The package of claim 1, wherein the filler consists essentially of carbon black.

10. A package for a prepasted orthodontic bracket, comprising:

a cover, including a hollow projection therein and a lateral flange extending from and surrounding an open end of the projection;

a base having a flat upper surface; and an orthodontic bracket having a layer of light-curable paste thereon, which bracket is placed with the paste layer in contact with a flat upper surface of the base, and the bracket is surrounded by and spaced from the cover, wherein each of the cover and base are opaque to visible light and actinic radiation, and wherein the cover comprises a plastic structure including a plastic material having dispersed therein (a) particles of an opaque filler in an amount effective to render the structure opaque to visible light, and (b) an effective amount of an actinic blocking agent.

11. A multi package for prepasted orthodontic brackets, comprising:

a cover, including a series of spaced hollow projections thereon and a lateral flange extending from and surrounding open ends of the projections;

a base having a flat upper surface;

a series of orthodontic brackets each having a layer of light-curable paste thereon, which brackets are placed in spaced positions with the paste layer in contact with a flat upper surface of the base, so that each bracket is disposed inside a hollow projection of the cover; and a releasable adhesive layer formed on an undersurface of the flange, which adhesive layer secures the cover to the base, wherein each of the cover and base are opaque to visible light and actinic radiation, and wherein the cover comprises a bilayered plastic structure including a first plastic layer containing particles of an opaque filler in an amount effective to render the first layer opaque to visible light, and a second plastic layer containing an effective amount of an actinic blocking agent.

12. The multi package of claim 11, wherein each of the cover and base have two or more alignable registration holes therein.

13. The multi package of claim 11, further comprising a series of transverse lines of weakness permitting an individual bracket container to be torn off of the package.

14. The multi package of claim 11, wherein the multi package comprises a flexible tape that can be wound.

\* \* \* \* \*